(12) United States Patent
Bonrath

(10) Patent No.: US 9,415,374 B2
(45) Date of Patent: Aug. 16, 2016

(54) DEVICE USEFUL FOR HYDROGENATION REACTIONS (III)

(71) Applicant: DSM IP ASSETS B.V., Heerlen (NL)

(72) Inventor: Werner Bonrath, Basel (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 14/395,150

(22) PCT Filed: Apr. 17, 2013

(86) PCT No.: PCT/EP2013/057950
§ 371 (c)(1),
(2) Date: Oct. 17, 2014

(87) PCT Pub. No.: WO2013/156501
PCT Pub. Date: Oct. 24, 2013

(65) Prior Publication Data
US 2015/0105580 A1    Apr. 16, 2015

(30) Foreign Application Priority Data
Apr. 18, 2012 (EP) .................... 12164528

(51) Int. Cl.
C07C 33/02    (2006.01)
B01J 19/24    (2006.01)
(Continued)

(52) U.S. Cl.
CPC ............... *B01J 23/44* (2013.01); *B01J 10/007* (2013.01); *B01J 12/007* (2013.01); *B01J 19/0093* (2013.01); *B01J 19/02* (2013.01); *B01J 19/2415* (2013.01); *B01J 19/2485* (2013.01); *B01J 23/60* (2013.01); *B01J 23/883* (2013.01); *B01J 23/885* (2013.01); *B01J 23/8876* (2013.01); *B01J 23/8878* (2013.01); *B01J 23/8892* (2013.01); *B01J 23/8993* (2013.01); *B01J 35/006* (2013.01); *B01J 35/0006* (2013.01); *B01J 35/04* (2013.01); *B01J 37/0201* (2013.01); *C07C 29/17* (2013.01); *C07C 67/283* (2013.01); *C10G 3/47* (2013.01); *C10G 3/50* (2013.01); *C10G 45/40* (2013.01); *B01J 21/04* (2013.01); *B01J 23/06* (2013.01); *B01J 2219/0086* (2013.01); *B01J 2219/00094* (2013.01);
(Continued)

(58) Field of Classification Search
CPC ........ B01J 23/44; B01J 10/007; B01J 12/007; C07C 29/17; C07C 67/283
USPC ...................................................... 560/261
See application file for complete search history.

(56) References Cited

FOREIGN PATENT DOCUMENTS

CH    WO 2010142809 A1 * 12/2010 ............... B01J 19/24
WO    WO 00/41804    7/2000
(Continued)

OTHER PUBLICATIONS

International Search Report for PCT/EP2013/057950 mailed Aug. 5, 2013.
(Continued)

Primary Examiner — Kamal Saeed
Assistant Examiner — Janet L Coppins
(74) Attorney, Agent, or Firm — Nixon & Vanderhye P.C.

(57) ABSTRACT

The present invention relates to a device for treatment of material transported through the device comprising at least one porous element consisting of specific solid metallic structure which allows cross-flow of the material through the porous element and wherein the porous element is coated by a non-acidic metal oxide which is impregnated by palladium (Pd).

14 Claims, 1 Drawing Sheet

(51) Int. Cl.
| | |
|---|---|
| *B01J 23/44* | (2006.01) |
| *B01J 10/00* | (2006.01) |
| *B01J 12/00* | (2006.01) |
| *B01J 19/00* | (2006.01) |
| *B01J 19/02* | (2006.01) |
| *B01J 35/00* | (2006.01) |
| *B01J 35/04* | (2006.01) |
| *C07C 29/17* | (2006.01) |
| *C10G 45/40* | (2006.01) |
| *B01J 23/889* | (2006.01) |
| *B01J 23/883* | (2006.01) |
| *B01J 23/885* | (2006.01) |
| *B01J 23/887* | (2006.01) |
| *B01J 23/89* | (2006.01) |
| *B01J 37/02* | (2006.01) |
| *C07C 67/283* | (2006.01) |
| *C10G 3/00* | (2006.01) |
| *B01J 23/60* | (2006.01) |
| *B01J 21/04* | (2006.01) |
| *B01J 23/06* | (2006.01) |

(52) U.S. Cl.
CPC ............ *B01J 2219/00792* (2013.01); *B01J 2219/00822* (2013.01); *B01J 2219/00824* (2013.01); *B01J 2219/00835* (2013.01); *B01J 2219/00873* (2013.01); *B01J 2219/0277* (2013.01); *B01J 2219/2403* (2013.01); *B01J 2219/2411* (2013.01); *B01J 2219/2428* (2013.01); *B01J 2219/2435* (2013.01); *B01J 2219/2437* (2013.01); *B01J 2219/2444* (2013.01); *Y02P 30/20* (2015.11)

(56) References Cited

FOREIGN PATENT DOCUMENTS

| | | | |
|---|---|---|---|
| WO | WO 2005/030390 | 4/2005 | |
| WO | WO 2008/101603 | 8/2008 | |
| WO | 2010-142809 | * 6/2010 | ............ B01J 19/24 |
| WO | WO 2010/142806 | 12/2010 | |
| WO | WO 2010/142809 | 12/2010 | |
| WO | WO 2012/001166 | 1/2012 | |

OTHER PUBLICATIONS

Written Opinion of the International Searching Authority for PCT/EP2013/057950 mailed Aug. 5, 2013.

C. Hutter et al., "Axial Dispersion in Metal Forms and Streamwise-Periodic Porous Media" Chemical Engineering Science, vol. 66, No. 6, Dec. 14, 2010, pp. 1132-1141.

C. Hutter et al., "Large Eddy Simulation of Flow Through a Streamwise-Periodic Structure", Chemical Engineering Science, vol. 66, No. 3, Feb. 1, 2011, pp. 519-529.

C. Hutter et al., "Heat Transfer in Metal Foams and Designed Porous Media", Chemical Engineering Science, vol. 66, No. 17, May 2, 2011, pp. 3806-3814.

* cited by examiner

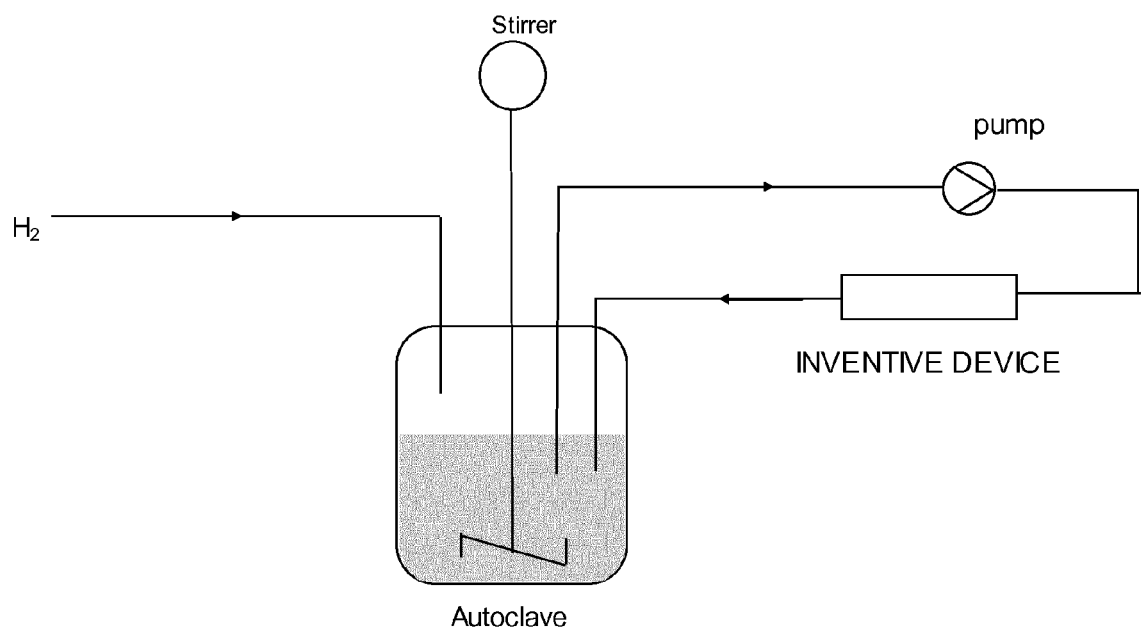

DEVICE USEFUL FOR HYDROGENATION REACTIONS (III)

This application is the U.S. national phase of International Application No. PCT/EP2013/057950 filed 17 Apr. 2013 which designated the U.S. and claims priority to EP 12164528.7 filed 18 Apr. 2012, the entire contents of each of which are hereby incorporated by reference.

The present invention relates to a device for treatment of material transported through the device comprising at least one porous element consisting of specific solid metallic structure which allows cross-flow of the material through the porous element and wherein the porous element is coated by a non-acidic metal oxide which is impregnated by palladium (Pd).

A device in accordance with the invention is useful to carry out chemical reactions under homogenous and heterogeneous conditions.

The device is useful for chemical reactions (especially hydrogenations, such as selective hydrogenations) in laboratory scale as well as in industrial scale.

WO2010/142806 and WO2010/142809 are disclosing similar devices useful as a mixer or heat exchanger for fluid or fluidized material transported through such a device. This device is also useful to carry out chemical reactions under homogenous and heterogeneous conditions.

The goal of the present invention was to provide devices with improved properties (especially in the view of selective hydrogenations), which are also easy to produce.

The device according to the present invention is also very stable (in regard to reaction conditions (such as pH), the substrates and the solvents (especially water)). The device is reusable very easily.

In particular, the device according to the invention comprises a tube having a wall, preferably a cylindrical wall, with at least one inlet end and at least one outlet end, wherein in the tube at least one porous element consisting of a solid foamy structure is arranged, wherein the porous element comprises a plurality of hollow spaces that are connected to each other and form an interconnected network, and wherein the at least one element is consisting of a specific metal alloy, which is then coated by a non-acidic metal oxide, which is then also impregnated by Pd, and wherein the at least one element and the wall are made in one piece.

The device and the at least one porous element may be manufactured in one piece by Selective Laser Sintering (SLS) a method described for example in U.S. Pat. Nos. 5,639,070, 5,732,323 and 6,676,892 or by Electron Beam Melting (EBM).

EBM process has some advantages which are as follows:
No thermal treatment
Smoother surfaces available than via SLS
2-3 times faster than SLS.

The present invention relates to a device for treatment of material transported through the device comprising at least one porous element consisting of specific solid metallic structure which allows cross-flow of the material through the porous element and wherein the porous element wherein is made from a metal alloy comprising wherein the main components of the metal alloy are cobalt (Co), chromium (Cr) and molybdenum (Mo).

Therefore the present invention relates to a device wherein the at least one porous element is made from a metal alloy comprising
(i) 55 weight-% (wt-%)—80 wt-%, based on the total weight of the metal alloy, of Co, and
(ii) 20 wt-%—40 wt-%, based on the total weight of the metal alloy, of Cr, and
(iii) 2 wt-%—10 wt-%, based on the total weight of the metal alloy, of Mo, and
wherein the porous element is coated by a non-acidic metal oxide and which is impregnated by palladium (Pd).

It is obvious that all percentages always add to 100.

The metal alloys used as a carrier are known as cobalt/chromium/molybdenum alloy. Such alloys are available commercially, i.e. from EOS GmbH Germany, from Attenborough Dental UK (Megallium®) and from International Nickel.

Such alloys are usually used in the field of dentistry. Especially, they are used in the production of dental prostheses.

Therefore it is surprising that such materials have excellent properties, when used as such devices according to the present invention.

Therefore the present invention relates to a device wherein the at least one porous element is made from a metal alloy comprising
(i) 55 wt-%—70 wt-%, based on the total weight of the metal alloy, of Co, and
(ii) 20 wt-%—35 wt-%, based on the total weight of the metal alloy, of Cr, and
(iii) 4 wt-%—10 wt-%, based on the total weight of the metal alloy, of Mo, and
wherein the porous element is coated by a non-acidic metal oxide layer and impregnated with Pd.

The metal alloy can comprise further metals, such as i.e. Cu, Fe, Ni, Mn, Si, Ti, Al and Nb.

An essential feature of the embodiment of the present invention is that the at least one porous element is coated by a non-acidic metal oxide layer.

The non-acidic metal oxide layer, which coats the at least one porous element, is basic or amphoteric. Suitable non-acidic metal oxide layers comprise Zn, Cr, Mn, Cu or Al. Preferably the oxide layer comprise ZnO and optionally at least one further metal oxide wherein the metal is chosen from the group consisting of Cr, Mn, Mg, Cu and Al.

The at least one element is preferably coated with a thin layer of ZnO and optionally at least one further metal (Cr, Mn, Mg, Cu and Al) oxide.

The coating of the metal alloy is done by commonly known processes, such as i.e. dip-coating.

Usually the device of the present invention comprises between 0.001 and 2 wt-%, based on the total weight of the catalyst, of ZnO, preferably between 0.01 and 1 wt-%.

In a preferred embodiment of the present invention the non-acidic metal oxide layers comprises ZnO and at least one further metal oxide wherein the metal is chosen from the group consisting of Cr, Mn, Mg, Cu and Al.

In a more preferred embodiment of the present the non-acidic metal oxide layer comprises ZnO and $Al_2O_3$.

When a mixture of ZnO and $Al_2O_3$ is used then it is preferred that the ratio of ZnO:$Al_2O_3$ is from 2:1 to 1:2.

The so coated element or elements are then impregnated by Pd-nanoparticles. The nanoparticles are synthesized by commonly known methods, i.e. by using $PdCl_2$ as a precursor, which is then reduced by hydrogen.

Usually the Pd-nanoparticles, which are on the non-acidic metal oxide layer, have an average particle size of between 0.5 and 20 nm, preferably of between 2 and 15 nm, more preferably of between 5 and 12 nm and most preferably of between 7 to 10 nm. (The size is measured by light scattering methods).

The device according to present invention comprises between 0.0001 and 1 wt-%, based on the total weight of the catalyst, of the Pd-nanoparticles, preferably between 0.001 and 0.1 wt-%.

In accordance with a further embodiment of the device, the hollow spaces of the at least one porous element are substantially sphere-shaped and have an average equivalent diameter of 0.5 to 20 mm, preferably of 1 to 10 mm, more preferably of 1.5 to 5 mm.

The shell which defines the surface area of the sphere-shaped hollow spaces further comprises a plurality of interconnecting holes which allow cross flow of the material. The average equivalent diameter of said holes is in the range of 0.01 to 5 mm, preferably in the range of 0.1 to 5 mm, more preferably in the range of 0.1 to 2 mm.

In a particular embodiment of the invention, the shell is manufactured such that it comprises a smooth or rough or partially smooth and partially rough surface.

In a preferred embodiment, the device is designed for the use as a mixer or heat exchanger or for the continuous handling of single and multiphase chemical reactions, as for example fast, exothermic, mixing sensitive or temperature sensitive reactions. The device provides a fast mixing of reactants and an extremely enhanced heat transfer. The fixed connection of the porous structure to the wall of the reactor is of major importance to guarantee a good heat transfer and very high mechanical stability. This enables the possibility to process up to high temperatures and pressures. The structure of the porous element has also a strong influence on the axial dispersion, the residence time distribution in the reactor respectively, which is an important parameter for the scaling of chemical plants.

For conventional batch reactors, which are often used in chemical plants, the energy dissipation may be controlled by the rotational speed of the stirrer. For continuous systems only the flow rate can be changed which is directly linked to the residence time and its distribution. This correlation is a disadvantage compared to batch reactors, but can be handled by clearly defined geometry of the porous elements designed by the aid of Computational Fluid Dynamics (CFD) which are then manufactured, e.g. by the SLS method mentioned above.

Hydrogenation of functional groups in organic molecules are examples of fast multiphase, exothermic reactions. Such reactions are part of environmentally acceptable reaction routes available for organic synthesis. For example, the precursors, i.e. intermediates for Vitamin A and Vitamin E are produced by three major types of reactions. One among them is catalytic selective hydrogenation, a multiphase, i.e. three-phase reaction, in which the reaction mixture comprises a liquid phase, a non-dissolved solid catalytic phase and a gaseous phase.

The most common reactor type for carrying out such hydrogenation reactions is the batch wise operated slurry reactor. Mainly stirred tanks and loop reactors are in use. Due to the strong exothermic reaction, a combination of external and internal heat exchangers is necessary for efficient temperature control. In addition, the concentration of catalysts used in the reaction is relatively low (<10%), which limits the reaction rate. Finally, the heat transfer performance of conventional reactors is in the order of 0.2 to 5 kW m$^{-3}$ K$^{-1}$. Therefore, large reactor volumes are necessary to get acceptable production rates.

The performance of hydrogenation processes and the product distribution is strongly influenced by the catalyst activity/selectivity and the interaction of chemical kinetics with transport phenomena in the reactor.

In three phase reactions one of the main problems to overcome is avoiding internal and external mass transfer limitations. Therefore, catalyst particles of small diameter are required. In technical application the minimal size, however, is limited due to catalyst handling like solids charging, filtration and discharging that often pose safety and environmental problems, and can lead to significant catalyst losses and economically unfavorable processes.

Further, as hydrogenations are highly exothermic, the removal of the reaction heat becomes the main limitation for the reactor performance. Therefore, in a slurry reactor the mass of the catalyst per volume is limited by its heat exchange capacity.

A further aspect concerns process safety and sustainable production under controlled pressure. Product intermediates in a multi-step chemical process as described above are often unstable and decompose releasing a huge amount of heat. The consequences are thermal runaway and explosion.

To increase the safety of the chemical reactions a strict heat management is required. In addition, the amount of reactants in the reactor should be as small as possible to reduce the hazard potential.

These problems of selective reactions may be solved by using a device hereinafter also referred to as plug flow reactor, design as defined by the invention. Such a reactor may be operated in a continuous mode. This operational mode avoids the storage of large quantities of unstable product intermediates as in the case of batch processes and increases the safety of chemical reactions.

This process integration is especially important to process thermal instable intermediates to stable ones.

The continuous plug flow reactor hereinafter described is optimized in its structured geometry in terms of heat and mass transfer. The plug flow like velocity field in the reactor guarantees an isothermal and homogeneous operating mode. It can be geometrically adapted to the heat transfer coefficients, viscosities, densities and the mixing behavior of the fluids used by the chemical reaction to optimize the ratio of operating expense (pressure drop, heating energy etc) and product quality (selectivity, conversion etc.). On the other hand, the structure of the at least one porous element fulfills not only the requirements of static mixing elements, it also acts as a flame arrestor for critical reactions and it permits mechanical and chemical stability of the continuous system through the convenient molding and the right choice of the material.

To fulfill all those requirements the geometry of the at least one porous element must not be consistent over the length of the element and can be adjusted to the different conditions. Furthermore and dependent on the reaction which takes place in the tube, the porous element may stretch across the whole length of the tube or may have a length of 10 to 90%, preferably 50 to 80%, of the total length of the reactor tube.

A plug flow reactor according to the invention has characteristic dimensions in the millimeter range. Preferably, the reactor is used with channel diameters between 0.5 and 300 mm.

In a preferred embodiment of the invention, the reactor tube has a diameter which is in the range of from 1 to 300 mm, preferably from 2 to 100 mm, more preferably from 5 to 50 mm.

With regard to the use of the device as reactor to carry out chemical reactions, it is a fundamental object within the scope of the present invention to propose the use of catalysts. In plug flow reactors, catalyst particles can be used as in traditional suspension reactors in mobilized or immobilized form. If the catalyst particles are used in immobilized, the preferably sintered metallic structure of the porous element(s) can act as a support for the catalysts.

Another main feature of the reactor is the high surface to volume ratio compared to traditional chemical reactors. The specific surface of the reactor established by the at least one porous element lies in the range of 500 to 50,000 $m^2\ m^{-3}$, whereas the specific surface in typical laboratory and production vessels is about 10 $m^2\ m^{-3}$ and very seldom exceeds 100 $m^2\ m^{-3}$.

In a preferred embodiment of a plug flow reactor, the tube comprises a double-walled cylindrical housing defining an annular chamber, wherein said annular chamber includes at least one fluid inlet and at least one fluid outlet which are connected to a heat exchanger for continuously transporting a heat exchange fluid through said chamber for cooling or heating the reaction mixture.

Alternatively or in combination with the double walled cylindrical housing, the tube may comprises a central inner-tube arranged in longitudinal direction of the cylindrical wall, wherein said inner tube includes at least an outlet for adding a compound of the reaction process to the material transported through the tube or it is arranged with an inner tube without an outlet for transporting a heat exchange fluid through the reactor.

In general the device according to the present invention is produced by
- (i) producing the device (including the at least one porous element) out of the metal alloy (especially EOS CobaltChrome MP1®), and
- (ii) coating the device (the inner part of it) by a non-acidic metal oxide layer, and
- (iii) impregnating the non-acidic metal oxide layer with Pd nanoparticles.

The device according to the present invention is used in selective catalytic hydrogenation of organic starting material, especially of organic starting material comprising a carbon-carbon triple bond, more especially of alkynol compounds. Therefore the present invention also relates to the use of a device according to the present invention in selective catalytic hydrogenation of organic starting material, especially of organic starting material comprising a carbon-carbon triple bond, more especially of alkynol compounds.

Preferably the present invention relates to a process of reacting a compound of formula (I)

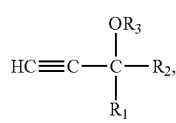
(I)

wherein
$R_1$ is linear or branched $C_1$-$C_{35}$ alkyl or linear or branched $C_5$-$C_{35}$ alkenyl moiety, wherein the C chain can be substituted, and
$R_2$ is linear or branched $C_1$-$C_4$ alkyl, wherein the C chain can be substituted,
$R_3$ is H or —C(CO)$C_1$-$C_4$alkyl,
with hydrogen whereas the reaction solution is pumped (or otherwise conveyed) through a device according to the present invention.

Hydrogen is usually used in the form $H_2$ gas.

Preferred compounds of formula (I) are the following:

(Ia)

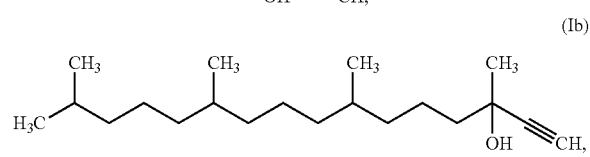
(Ib)

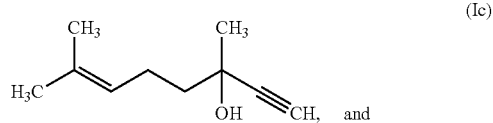
(Ic)

and

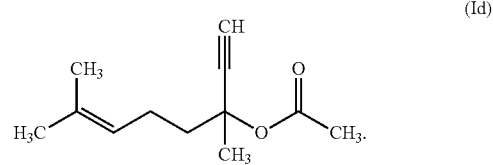
(Id)

They are hydrogenated to the corresponding compounds of formula (Ia'), (Ib'), (Ic') and (Id'):

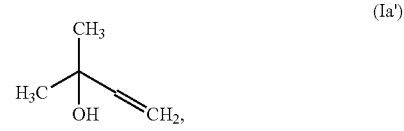
(Ia')

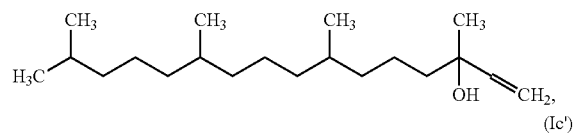
(Ib')

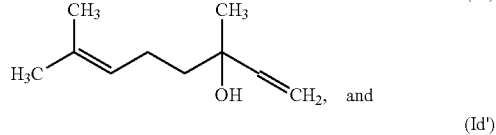
(Ic')

and

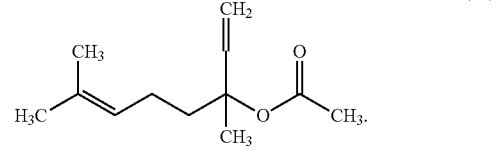
(Id')

The reaction is usually carried out under pressure. Usually between 2 and 10 bar.

The reaction is usually carried out at elevated temperature. Usually between 30° C. and 80° C.

The reaction is usually carried out without any solvents. But it is also possible to use solvents, which are inert to hydrogenation.

FIG. 1: shows a suitable arrangement of the hydrogenation process.

In the following, the invention will be described in more detail. All the parts are related to weight and the temperatures are given in ° C. if not otherwise mentioned.

EXAMPLE 1

Manufacturing of the Device (Plug Reactor)

In terms of chemical reactions in metal foamy structures some difficulties of commercially available foams had to be solved. On one hand, commercially available material, like aluminum or copper, is critical for chemical reactors, especially in terms of corrosion. On the other hand, the connection from the foam to the wall which is a limiting step in the heat transfer. Different approaches like soldering were tested but no persistent connection was achieved. Therefore and in accordance with the present invention a new manufacturing approach is proposed, which is the so called laser sintering technique (SLS), as described in the introduction. With this technology, a three-dimensional structure of nearly every shape can be designed in a Computer Assisted Design (CAD) software and than manufactured as one single part. This is done by depositing a layer of the metal powder (EOS CobaltChrome MP1®), directing energy on a selected position corresponding to the CAD model to sinter it before depositing a new layer and begin the procedure again as it is for example described in U.S. Pat. Nos. 5,639,070, 5,732,323 and 6,676,892. Because the manufacturing process has nearly no limitation in terms of geometry up to a length scale in the order of 50 μm every process specific design criteria can be fulfilled by the manufacturer. These preferences allow very precise scaling for chemical processing by adapting the most influential parameters listed in the following. An alternative approach would be the so called Electron Beam Melting (EBM) process which is also described in the introduction.

The device had a length of 200 mm, an outside diameter of 10 mm, an inside diameter of 6 mm and an empty volume of the tube or 4.4 ml.

Afterwards the device was coated with the metal oxide layer and then the Pd-nanoparticles have been deposited onto this layer.

Afterwards the device was subjected to a thermal pre-treatment at 450° C. for 3 h.

Deposition of ZnO+$Al_2O_3$ (Coating of the Porous Element)

Preparation of the $Al_2O_3$+ZnO Precursor Solution: To a 100 mL-flask was added $Al(NO_3)_3.9H_2O$ (20.0 g, 53.3 mMol) and water (70 mL). The mixture was stirred until $Al(NO_3)_3.9H_2O$ was dissolved completely. The solution was heated up to 95° C. Then ZnO powder (4.34 g, 53.3 mMol) was slowly added to the solution. Heating and stirring were maintained until ZnO was completely dissolved. The solution was then cooled down to room temperature and filtrated through a membrane filter.

The deposition of ZnO+$Al_2O_3$ was performed by rinsing the inside of the oxidized device with the precursor solution. The device was then dried at 60° C. at 125 mbar for 2 h followed by calcination at 450° C. for 1 h. This process was repeated 2 times.

Impregnation with Pd

Preparation of a Pd° suspension: Sodium molybdate dihydrate (79.5 mg, 0.329 mmol) and palladium(II) chloride anhydrous (53.0 mg, 0.299 mmol) were added in 30 mL of deionized water under heating (ca. 95° C.) and stirring. Heating and stirring were continued until complete evaporation of water (solid residue was formed). Afterwards, 30 mL of deionized water were added to the residue under stirring. The evaporation-dissolving cycle was repeated two times in order to completely dissolve $PdCl_2$. Finally, 50 mL of hot water were added to the solid residue. The deep brown solution was cooled down to room temperature and filtrated through a paper filter into a 100 mL cylinder. The filter was washed with water. The final volume of the precursor solution should be 60 mL.

The Pd° suspension was formed by bubbling hydrogen through the precursor solution for 1 h in a glass cylinder at room temperature.

The one end of device was closed with a rubber stopper and the reactor was filled with the obtained Pd° suspension and the liquid was slowly evaporated in a vertical position at 90° C. under reduced pressure. This process was repeated 3 times.

Before the hydrogenation the catalyst was activated by $H_2$.

The use of such device leads to selective hydrogenation with good selectivities.

A suitable arrangement for a hydrogenation process is shown in FIG. 1.

The invention claimed is:

1. A device for treatment of material transported through the device comprising at least one porous element which allows cross-flow of the material through the device, wherein
    the at least one porous element consists of a solid metallic structure which is coated by a non-acidic metal oxide layer impregnated with Pd-nanoparticles having an average particle size of between 0.5 and 20 nm, and wherein
    the at least one porous element is formed of a metal alloy comprising:
    (i) 55 wt-%—80 wt-%, based on total weight of the metal alloy, of Co,
    (ii) 20 wt-%—40 wt-%, based on total weight of the metal alloy, of Cr, and
    (iii) 2 wt-%—10 wt-%, based on total weight of the metal alloy, of Mo.

2. The device according to claim 1, wherein the metal alloy further comprises at least one metal selected from the group consisting of Cu, Fe, Ni, Mn, Si, Ti, Al and Nb.

3. The device according to claim 1, wherein the metal alloy comprises:
    (i) 55 wt-%—70 wt-%, based on total weight of the metal alloy, of Co,
    (ii) 20 wt-%—35 wt-%, based on total weight of the metal alloy, of Cr, and
    (i) 4 wt-%—10 wt-%, based on total weight of the metal alloy, of Mo.

4. The device according to claim 1, wherein the non-acidic metal oxide layer which coats the at least one porous element is basic or amphoteric.

5. The device according to claim 1, wherein the non-acidic oxide layer comprises ZnO and optionally at least one further oxide of a metal selected from the group consisting of Cr, Mn, Mg, Cu and Al.

6. The device according to claim 1, wherein the non-acidic metal oxide layer comprises ZnO and $Al_2O_3$.

7. The device according to claim 1, wherein the Pd-nanoparticles have an average particle size of between 2 and 15 nm.

8. The device according to claim 5, wherein the non-acidic metal oxide layer comprises ZnO in an amount between 0.001 and 2 wt-%, based on the total weight of the non-acidic metal oxide layer.

9. The device according to claim 1, wherein the Pd-nanoparticles are present in an amount between 0.0001 and 1 wt-%, based on total weight of the device.

10. The device according to claim 1, wherein the at least one porous element comprises substantially sphere-shaped hollow spaces having an average equivalent diameter of 0.5 to 20 mm.

11. The device according to claim 1, wherein the Pd nanoparticles have an average particle size of between 5 and 12 nm.

12. The device according to claim 1, wherein the Pd nanoparticles have an average particle size of between 7 and 10 nm.

13. The device according to claim 10, wherein the sphere shaped hollow spaces of the at least one porous element have an average equivalent diameter of 1 to 10 mm.

14. The device according to claim 10, wherein the sphere shaped hollow spaces of the at least one porous element have an average equivalent diameter of 1.5 to 5 mm.

\* \* \* \* \*